United States Patent
Lu et al.

(10) Patent No.: US 11,786,170 B2
(45) Date of Patent: Oct. 17, 2023

(54) NANOMATERIAL EPIDERMAL SENSORS

(71) Applicant: BOARD OF REGENTS, THE UNIVERSITY OF TEXAS SYSTEM, Austin, TX (US)

(72) Inventors: Nanshu Lu, Austin, TX (US); Deji Akinwande, Austin, TX (US); Shideh Kabiri Ameri Abootorabi, Austin, TX (US)

(73) Assignee: BOARD OF REGENTS, THE UNIVERSITY OF TEXAS SYSTEM, Austin, TX (US)

(*) Notice: Subject to any disclaimer, the term of this patent is extended or adjusted under 35 U.S.C. 154(b) by 841 days.

(21) Appl. No.: 16/608,994

(22) PCT Filed: Apr. 28, 2017

(86) PCT No.: PCT/US2017/030057
§ 371 (c)(1),
(2) Date: Oct. 28, 2019

(87) PCT Pub. No.: WO2018/199977
PCT Pub. Date: Nov. 1, 2018

(65) Prior Publication Data
US 2020/0054273 A1   Feb. 20, 2020

(51) Int. Cl.
*A61B 5/00* (2006.01)
*A61B 5/01* (2006.01)
(Continued)

(52) U.S. Cl.
CPC ............... *A61B 5/443* (2013.01); *A61B 5/01* (2013.01); *A61B 5/257* (2021.01); *A61B 5/28* (2021.01);
(Continued)

(58) Field of Classification Search
CPC .......... A61B 5/443; A61B 5/053; A61B 5/28; A61B 5/296; A61B 5/25; A61B 5/68335;
(Continued)

(56) References Cited

U.S. PATENT DOCUMENTS

2012/0261296 A1   10/2012   Tinsley
2013/0022811 A1   1/2013   Ahn et al.
(Continued)

FOREIGN PATENT DOCUMENTS

WO   2015148957   10/2015

OTHER PUBLICATIONS

Akinwande, Deji, Nicholas Petrone, and James Hone. "Two-dimensional flexible nanoelectronics." Nature communications 5 (2014): 5678.
(Continued)

*Primary Examiner* — Chu Chuan Liu
(74) *Attorney, Agent, or Firm* — Meunier Carlin & Curfman LLC

(57) ABSTRACT

Nanomaterial epidermal sensors can be adhered to the skin and worn comfortably and inconspicuously for days to allow for repeated biometric sensing. The nanomaterial epidermal sensors may be comprised of a monolayer of graphene coating a flexible polymer substrate. Various nanomaterial epidermal sensors may be quickly fabricated using a cost-efficient "cut-and-paste" method on transfer paper and can be adhered directly to skin without tape or adhesive, much like a temporary-tattoo. The nanomaterial epidermal sensors may be optically transparent and may be used to measure an electrocardiogram (ECG), an electroencephalogram (EEG) or an electromyogram (EMG) with a signal-to-noise ratio that is comparable to conventional electrodes. In addition, the nanomaterial epidermal sensors may be used to measure other parameters, such as skin temperature or skin hydration.

13 Claims, 5 Drawing Sheets

(51) Int. Cl.
  *A61B 5/291* (2021.01)
  *A61B 5/296* (2021.01)
  *A61B 5/28* (2021.01)
  *A61B 5/257* (2021.01)
(52) U.S. Cl.
  CPC .............. *A61B 5/291* (2021.01); *A61B 5/296* (2021.01); *A61B 5/68335* (2017.08); *A61B 2562/0285* (2013.01); *A61B 2562/125* (2013.01); *A61B 2562/164* (2013.01); *A61B 2562/222* (2013.01)
(58) Field of Classification Search
  CPC ........... A61B 5/257; A61B 5/291; A61B 5/01; A61B 5/259; A61B 5/282; A61B 2562/0261; A61B 2562/046; A61B 2562/164; A61B 2562/029; A61B 2562/222; A61B 2562/125; A61B 2562/0285; A61B 2562/066; A61B 2560/0428
  See application file for complete search history.

(56) References Cited

U.S. PATENT DOCUMENTS

| | | | |
|---|---|---|---|
| 2013/0041235 A1 | 2/2013 | Rogers et al. | |
| 2015/0126834 A1 | 5/2015 | Wang et al. | |
| 2015/0273737 A1 | 10/2015 | Chen et al. | |
| 2016/0007874 A1* | 1/2016 | Ma | A61B 5/6868 600/377 |
| 2017/0049612 A1* | 2/2017 | Hussain | A61F 7/007 |
| 2017/0136265 A1* | 5/2017 | Hyde | A61B 5/45 |
| 2017/0316487 A1* | 11/2017 | Mazed | G06Q 30/0241 |

OTHER PUBLICATIONS

Dagdeviren, Canan, et al. "Conformal piezoelectric systems for clinical and experimental characterization of soft tissue biomechanics." Nature materials 14.7 (2015): 728.

Huang, Xian, et al. "Epidermal differential impedance sensor for conformal skin hydration monitoring." Biointerphases 7.1 (2012): 52.
Huang, Xian, et al. "Stretchable, wireless sensors and functional substrates for epidermal characterization of sweat." Small 10.15 (2014): 3083-3090.
Jeong, et al. "Materials and optimized designs for human-machine interfaces via epidermal electronics," Advanced Materials, vol. 25, pp. 6839-6846, 2013.
Kim, Dae-Hyeong, et al. "Epidermal electronics." science 333.6044 (2011): 838-843.
Kim, Dae-Hyeong, et al. "Flexible and stretchable electronics for biointegrated devices." Annual review of biomedical engineering 14 (2012): 113-128.
Kuzum, Duygu, et al. "Transparent and flexible low noise graphene electrodes for simultaneous electrophysiology and neuroimaging." Nature communications 5 (2014): 5259.
Lanzara, Giulia, et al. "A Spider-Web-Like Highly Expandable Sensor Network for Multifunctional Materials." Advanced Materials 22.41 (2010): 4643-4648.
Li, Teng, et al. "Compliant thin film patterns of stiff materials as platforms for stretchable electronics." Journal of materials research 20.12 (2005): 3274-3277.
Wang, Liu, and Nanshu Lu. "Conformability of a thin elastic membrane laminated on a soft substrate with slightly wavy surface." Journal of Applied Mechanics 83.4 (2016): 041007.
Webb, R. Chad, et al. "Ultrathin conformal devices for precise and continuous thermal characterization of human skin." Nature materials 12.10 (2013): 938-944.
Widlund, Thomas, et al. "Stretchability and compliance of freestanding serpentine-shaped ribbons." International Journal of Solids and Structures 51.23-24 (2014): 4026-4037.
Yang, Shixuan, Eley Ng, and Nanshu Lu. "Indium Tin Oxide (ITO) serpentine ribbons on soft substrates stretched beyond 100%." Extreme Mechanics Letters 2 (2015): 37-45.
Yang, Shixuan, et al. ""Cut-and-Paste" Manufacture of Multiparametric Epidermal Sensor Systems." Advanced Materials 27.41 (2015): 6423-6430.
International Preliminary Report on Patentability issued for Application No. PTC/US2017/030057, dated Nov. 7, 2019.
International Search Report and Written Opinion in PCT/US2017/030057. dated Sep. 7, 2017. 24 pages.

* cited by examiner

NANOMATERIAL EPIDERMAL SENSORS

GOVERNMENT SUPPORT

This invention was made with government support under Grant No. 1541684 awarded by the National Science Foundation (NSF) and Grant No. N00014-16-1-2044 awarded by the Office of Naval Research (ONR). The government has certain rights in the invention.

FIELD OF THE INVENTION

The present invention relates to the field of wearable electronics and, more specifically, to nanomaterial sensors worn on skin for biometric sensing.

BACKGROUND

Physiological sensors mounted to the epidermis are important for mobile health and human-machine interaction. Conventional devices, such as a Holter monitor for measuring the electrical activity of a cardiovascular system and a MYO™ band for measuring the electrical activity of skeletal muscles are too bulky, rigid, constraining, and susceptible to motion artifacts for long-term ambulatory measurements.

A new class of epidermal sensors has emerged. These sensors are stretchable, softer, thinner, and less bulky, but despite these advantages, some drawbacks associated with skin-electrode impedance and motion artifacts still exist.

Low skin-electrode impedance is desirable and requires an epidermal sensor to conform to a microscopic surface roughness of an epidermis. This conformability may reduce electrode-skin interface impedance and hence reduce motion artifacts. One approach to enhance this conformability is to reduce the thickness of an epidermal sensor so that the bending stiffness is greatly reduced and the sensor can fully conform to the epidermis without using any adhesives.

The use of thin and serpentine-shaped bilayers of gold films on polyethylene terephthalate or polyimide sheets as conductive electrodes has been demonstrated for epidermal sensors. For example, the total thickness of the bilayer may be 1.2-25 microns and the gold layer may be 100 nanometers. Despite the reduced thickness, these sensors can still lose contact with the skin when it wrinkles. Improvements in skin compatibility, wear-ability, and performance could be made with this thickness pushed even thinner; however, the fabrication of serpentine-shaped gold membranes is costly and time consuming because the fabrication process requires a clean room and complex equipment and techniques. What is more, these sensor systems require adhesives, which can be irritating to some test subjects and can limit the breathability of human skin. Finally, these sensors are not transparent, which may make a test subject uncomfortable when wearing these sensors (e.g., on their face or hands) and which may make optical testing of the epidermis in the region of the sensor system impossible.

A need, therefore, exists for an ultra-thin epidermal sensor that does not require adhesives/tape, is conformable to the epidermis, is invisible to a wearer, is fabricated easily/inexpensively, and performs at least as well as conventional sensors systems in physiological measurements.

SUMMARY

Accordingly, in one aspect, the present disclosure embraces an epidermal electrode. The epidermal electrode includes a flexible and transparent polymer substrate coated with a layer of graphene. The epidermal electrode also includes a sheet of transfer paper. The transfer paper is bonded to the flexible polymer substrate using a water-soluble glue. When the layer of graphene is placed against an epidermis and the sheet of transfer paper is moistened, the flexible polymer substrate is released from the sheet of transfer paper and the graphene layer is adhered to the epidermis.

In possible embodiments of the epidermal electrode, a layer of polymathic methacrylate (PMMA) is coated with a thin layer of graphene that is less than 1 nanometer (nm) thick to form a graphene coated PMMA structure that is less than 500 nm thick, that has a mass density (e.g., ~1.18 g/cm$^3$) comparable to an epidermis (e.g., ~1.09 g/cm$^3$), and that is optically transparent (e.g., at visible and NIR wavelengths). In some cases, the PMMA coated with graphene is cut to form a stretchable pattern.

In another aspect, the present disclosure embraces a method for preparing an epidermal electrode. The method starts by growing graphene on a substrate. The graphene on the substrate is then coated with a sheet of polymer. The substrate is then removed so that what remains is a polymer-graphene sheet that has a graphene side and a polymer side. The polymer side of the polymer-graphene sheet is adhered to a transfer material to form a decal that has a graphene side and a transfer material side. The polymer-graphene sheet is then adhered to an epidermis by applying the graphene side of the decal to the epidermis and removing the transfer material from the decal.

In some possible embodiments of the method, the graphene is gown onto a sheet of copper foil using atmospheric pressure chemical vapor deposition (APCVD). The graphene is then coated with a sheet of polymer by spin-coating and baking the polymer onto the graphene. The copper foil may then be etched away leaving only the polymer-graphene sheet with a thickness of less than 500 nm. The polymer side of the polymer-graphene sheet is then adhered to a sheet of transfer paper. The polymer-graphene sheet is then cut and extraneous portions are removed to form a polymer-graphene pattern on the transfer paper. The polymer-graphene pattern (i.e., pattern) forms the electrode. Accordingly, the pattern includes a plurality of contacts (e.g., disc-shaped contacts) for electrical connection. Each of the contacts may be spatially separated and/or connected by a trace that follows a serpentine path. The electrode may be applied to the epidermis by moistening the sheet of transfer paper to release the polymer-graphene pattern from the transfer paper (i.e., like a decal or transfer tattoo), pressing the polymer-graphene pattern to the epidermis, and peeling the moistened sheet of transfer paper away from the polymer-graphene pattern, which remains adhered to the epidermis due to a van der Waals force.

In another aspect, the present disclosure embraces a graphene epidermal sensor system (GESS). The GESS includes a flexible polymer substrate coated with a monolayer of graphene that is cut into a graphene electrode/sensor pattern, which is adhered to an epidermis of a test subject by van der Waals forces. The GESS also includes electrical leads that are connected to the graphene electrode pattern to transmit and/or receive electrical signals to and/or from the test subject. The GESS also includes test equipment connected to the electrical leads that sense a biological parameter or measure a biological signal corresponding to the test subject.

The graphene electrode pattern may have a variety of configurations for measuring various biological parameters or biological signals. In a possible embodiment, the graphene electrode pattern includes two contacts that are connected by a serpentine trace. The serpentine trace forms a resistance temperature detector (RTD) and test equipment attached (via electrical leads) to the contacts of the RTD may measure skin temperature. In another possible embodiment, the graphene electrode pattern forms a skin hydration sensor (SHS) and test equipment attached (via electrical leads) to the contacts of the SHS may measure skin hydration. In another possible embodiment, the graphene electrode pattern forms an electrophysiological sensor (EPS) and test equipment attached (via electrical leads) to the contacts of the EPS may measure biological signals for a variety of applications. For example, the EPS may measure biological signals for electroencephalography (EEG), electrocardiography (ECG), and/or electromyography (EMG).

In possible implementations, the graphene electrode pattern remains adhered to the epidermis of a test subject for an extended period, such as days. Accordingly, the electrical leads and test equipment may be attached, disconnected, and reattached multiple times during the period for repeated measurements.

In another aspect, the present disclosure embraces a method for using a GESS. The method includes adhering a graphene electrode pattern to an epidermis of a subject. The graphene electrode pattern includes a plurality of contacts consisting of a flexible polymer substrate coated with a monolayer of graphene. The method further includes connecting electrical leads to two or more of the contacts and transmitting/receiving electrical signals to/from the electrical leads to sense an attribute of the epidermis or an electrophysiological signal.

In an exemplary embodiment of the method, the sensed attribute of the epidermis is a hydration level, which is sensed by measuring an impedance between two contacts of the graphene electrode pattern.

In another exemplary embodiment of the method, the sensed attribute of the epidermis is a temperature, which is sensed by measuring an impedance of an RTD between two contacts of the graphene electrode pattern. In some cases, the RTD is embodied as a serpentine trace connecting the two contacts.

In other exemplary embodiments of the method, the sensed electrophysiological signal is an ECG, EEG, and/or EMG.

In another exemplary embodiment of the method, connecting electrical leads to two or more of the plurality of contacts includes aligning the electrical leads with one or more alignment features, which are one or more shapes, patterns, and/or openings in the graphene electrode pattern.

In another exemplary embodiment of the method, the flexible polymer substrate is polyimide (PI).

The foregoing illustrative summary, as well as other exemplary objectives and/or advantages of the invention, and the manner in which the same are accomplished, are further explained within the following detailed description and its accompanying drawings.

DETAILED DESCRIPTION

The present disclosure embraces a nanomaterial epidermal electrode (i.e., electrode, electrode decal, graphene electrode, electrode tattoo) for biometric sensing that is inexpensive to fabricate, can be easily adhered to the skin, can be worn comfortably and inconspicuously for days, and that is disposable. The present disclosure also embraces methods to prepare and use the electrode. Finally, the present disclosure embraces sensor systems that utilize the electrode to measure various biological parameters and signals.

The electrode disclosed herein is ultrathin (e.g., less than or equal to 500 nanometers thick), transparent (e.g., greater than or equal to 85%), and stretchable (e.g., approximately 50%). The electrode is fabricated using a low-cost "wet transfer, dry patterning" process. The electrode can be applied directly on human skin (i.e., like a temporary transfer tattoo). After applied, the electrode can remain attached and conform to microscopic skin surface morphologies without tape or adhesives due to a van der Waals force. The electrode may be imperceptible to a wearer and is adaptable to arbitrary skin deformations without fracture or delamination. The electrode can be worn on the skin for days (e.g., 4 days when covered with a liquid bandage). The electrode may be used to measure an electrocardiogram (ECG), an electromyogram (EMG), and electroencephalogram (EEG), skin temperature, and skin hydration. The electrode-skin impedance, signal-to-noise ratio (SNR) and motion artifacts of the electrode are comparable to commercially available silver/silver-chloride (Ag/AgCl) gel electrodes. Further, when the electrode is compared to commercially available dry electrodes the compared improvements in electrode-skin interface impedance, SNR, and motion artifacts are even larger.

The method for preparing the electrode disclosed herein does not require photolithography or its associated complexity and expense. The disclosed process may be completed in an ambient environment and protects the nanomaterial from being contaminated by chemicals as they would in a photolithography process.

Figure 1:
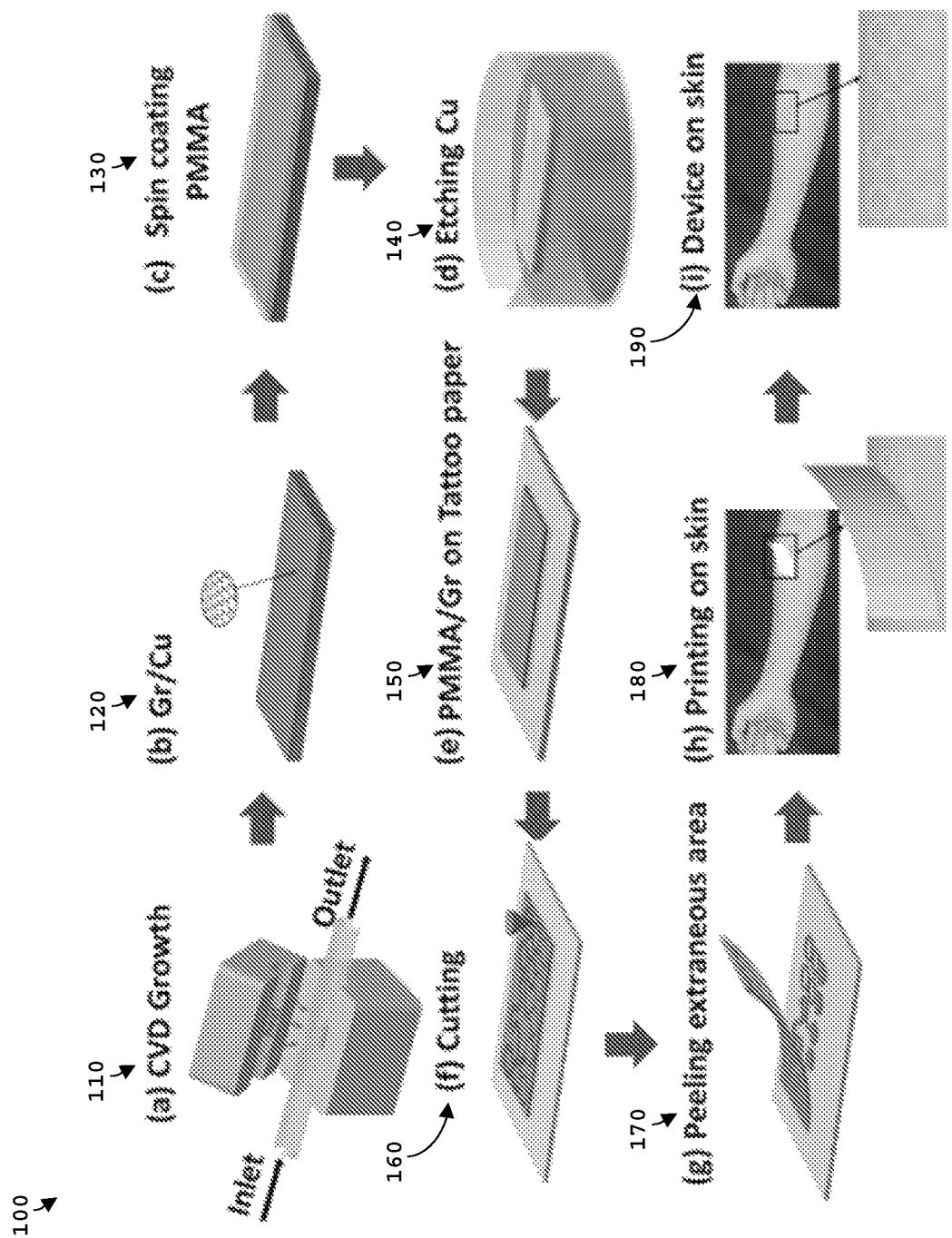
FIG. 1 graphically depicts the operations and flow of a method for preparing an epidermal electrode according to an embodiment of the present disclosure.

A flow chart of the method 100 for preparing the electrode (i.e., epidermal electrode, epidermal electrode decal, graphene electrode pattern, electrode, sensor, etc.) is graphically illustrated in FIG. 1.

The electrode uses a nanomaterial as a conductor because it is can be gown ultra-thin while remaining electrically conductive, optically transparent, and mechanically robust. Graphene nanomaterial sensors are the subject of the present disclosure but the disclosure anticipates that other nanomaterials may also be used (e.g., molybdenum disulfide).

A graphene layer (e.g., monolayer) can be gown 110 on a substrate, which is typically a sheet of copper foil. The operation of growing 110 can be performed using chemical vapor deposition (CVD) at atmospheric pressure. The process of atmospheric pressure chemical deposition (APCVD) may include heating the copper at 1030 degrees Celsius (° C.) while flowing hydrogen at 10 standard cubic centimeters per minute (sccm) for 15 minutes (min) to treat the copper surface and flowing methane at 2 sccm for 10 min to grow a layer (e.g., monolayer) of graphene on the copper. During the growth process, Argon can be flowed at 300 sccm to maintain atmospheric pressure. The results of the growth 110 is a layer of graphene on the copper substrate (i.e., Gr/Cu) 120. The graphene-coated copper 120 has a copper side (lower side as shown) and a graphene side (upper side as shown).

A layer of polymer may be spin coated 130 onto the graphene side of the graphene-coated copper 120. The coated polymer layer is typically a flexible and transparent polymer, such as polymethyl methacrylate (PMMA) or polyimide (PI). Typically, PMMA is used because it can be spin coated to a form a layer that is less than 500 nm thick (e.g., 463 nm). The layer of PMMA may be spin coated at 3000 revolutions per minute (rpm) onto the graphene side of the graphene coated copper and then baked for 2 minutes (min.) at 180° C.

The copper can be etched 140 away (i.e., removed) using copper etchant to leave a flexible polymer substrate coated with a layer of graphene (i.e., polymer-graphene sheet, PMMA/Gr) that has a graphene side and a polymer side.

A sheet of transfer material (e.g., transfer paper) is then bonded 150 (e.g., using a water-soluble glue) to the polymer side of the polymer-graphene sheet to form a decal (i.e., temporary tattoo). The transfer material is typically transfer paper (e.g., SILHOUETTE™ tattoo paper), as used for decals or temporary tattoos.

The polymer-graphene sheet may be cut 160 using a mechanical cutter plotter (e.g., SILHOUETTE CAMEO®). The excess from the cutting can then be removed 170 from the transfer paper to form a transferrable graphene electrode pattern (i.e., pattern).

Water may then be applied to the transfer paper to facilitate the release of the graphene electrode pattern. The graphene electrode pattern (graphene side) is then pressed against an epidermis to adhere 180 the graphene electrode pattern to the epidermis (i.e., skin). The electrode is adhered to the skin via a van der Waals force (i.e., interaction) so no adhesives or tape is necessary.

The transfer paper is peeled 190 from the adhered pattern on the skin to complete the transfer of the graphene electrode to the epidermis.

The graphene electrode pattern (i.e., epidermal electrode) may be configured in a variety of ways to adapt to the skin and to couple electrical signals to/from the test subject. For example, the shape of the epidermal electrode may be configured to sketch a wrinkle with the skin without losing contact and while minimizing motion artifacts. In another example, the epidermal electrode may be configured to maximize surface area and minimize interface impedance.

Figure 2:
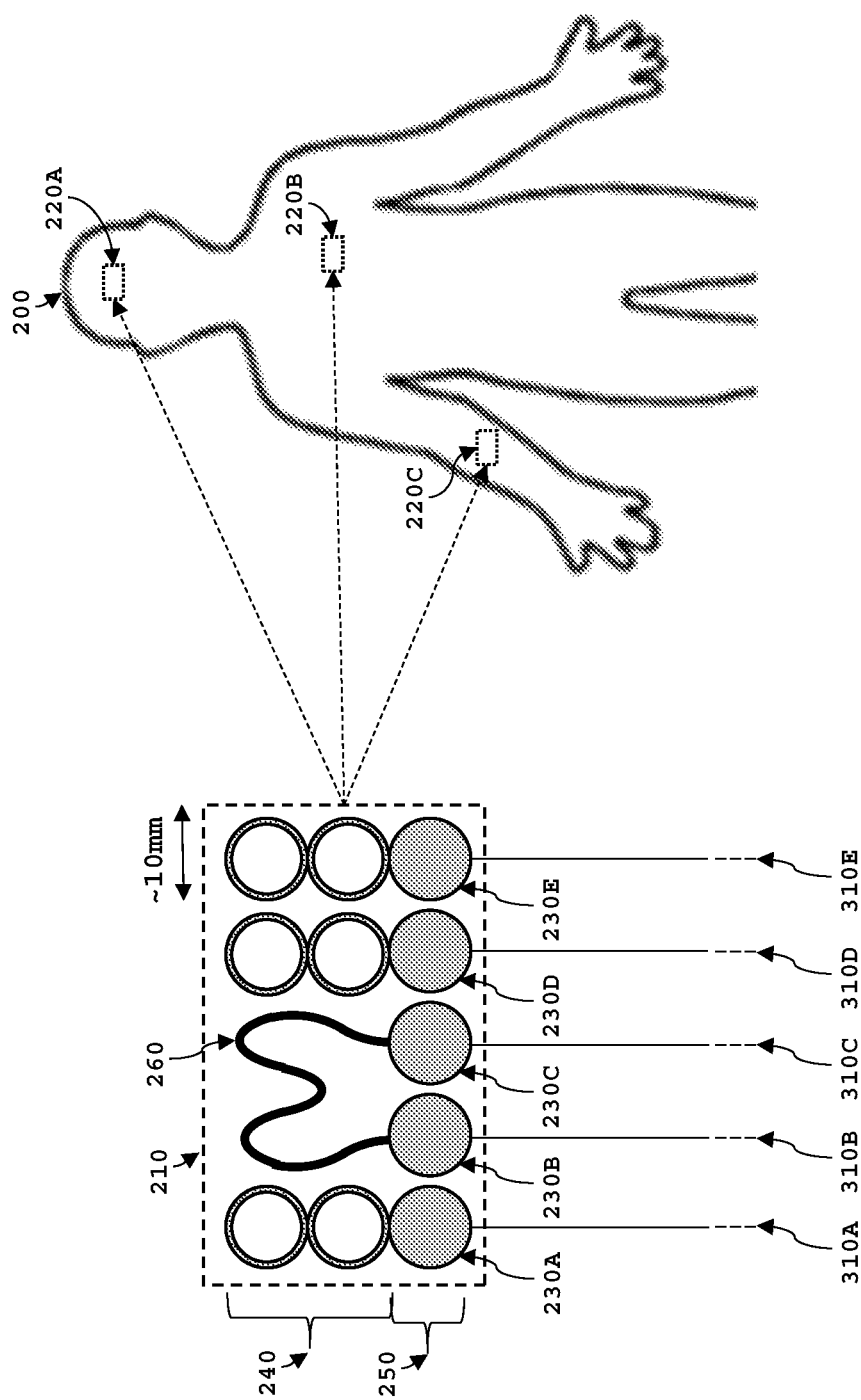
FIG. 2 graphically depicts an epidermal electrode according to an embodiment of the present disclosure and several possible locations on a human subject on which the epidermal electrode may be adhered.

An exemplary epidermal electrode 210 (i.e., electrode) is shown in FIG. 2. The epidermal electrode may be adhered to various places on a test subject 200 depending on the desired sensing. For example, an electrode 210 may be applied to the test subject's chest 220B to measure an ECG. In another example, the electrode 210 may be applied to the test subject's forehead 220A to measure an EEG. In another example, the electrode 210 may be applied to the test subject's forearm 220C to measure EMG. These examples are not intended to be limiting. It is envisioned that the epidermal electrode may be applied to any part of the test subject's body. Further, the test subject may human or non-human.

The epidermal electrode 210 may include a plurality of contacts 230A-E for sensing various biological parameters and/or signals. The contacts 230A-E may have a variety of shapes and sizes. As shown in FIG. 2, the epidermal electrode has five contacts 230A-E that are each approximately 10 millimeters (mm) wide and that are spatially separated by a few millimeters. The contacts 230A-E typically include a disc shaped pad portion 250 (i.e., pad) for connection to an electrical lead 310A-E. The pad is typically shaped/sized to match an electrical lead to minimize impedance at the interface. The contacts 230A-E may also include a trace portion 240. The trace portion 240 may have a serpentine shape and may connect pads from two different contacts (e.g., the serpentine trace 260 as shown in FIG. 2). Alternatively, a trace portion may have a serpentine shape and may depart from and return to the same pad after tracing some shape (e.g., the two rings as shown in FIG. 2). The shape/configuration of the trace portion may be chosen to optimize the sensing (e.g., sensitivity, signal-to-noise, etc.). Further, the shape/configuration may also include alignment features to facilitate a connection and/or improve contact with electrical leads. The alignment features may include shapes, patterns, and/or openings in the graphene electrode pattern.

A graphene epidermal sensor system (GESS) is formed by connecting the graphene electrode's contacts 210A-E to electrical leads 310A-E, which are in turn, coupled to one or more pieces of test equipment (e.g., voltmeter, ohm meter, current meter, ECG meter, EMG meter, EEG meter, etc.). The GESS can be used to sense a variety of biological parameters (e.g., attribute of the epidermis) or biological signals (i.e., electrophysiological signal).

Figure 3:
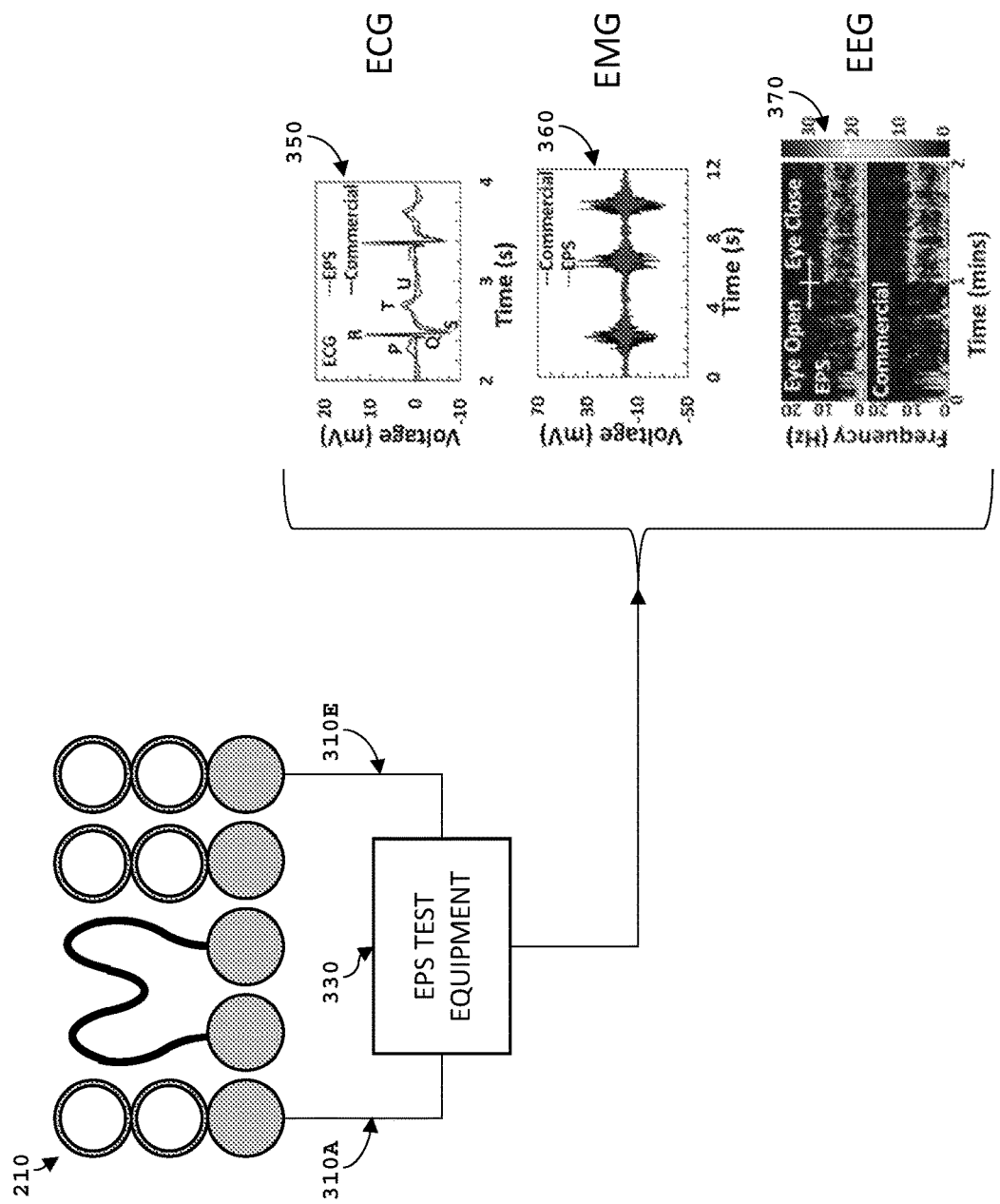
FIG. 3 graphically illustrates a graphene epidermal sensor system for measuring various electrophysiological signals according to an implementation of the present disclosure.

FIG. 3 graphically illustrates a GESS for measuring several exemplary electrophysiological signals (e.g., ECG, EMG, and EEG) according to an implementation of the present disclosure.

In a first example, to measure an ECG 350, the graphene electrode is adhered to the chest 220B of a test subject 200. Electrical leads 310A,E are connected between the two outermost contacts 230A,E of the graphene electrode and an AVATAR™ recorder acting as the EPS test equipment 330. The ECG 350 measured using a graphene epidermal electrode (i.e., graphene electrode) and a commercially available gel electrode are shown to provide comparable results. The characteristic P, Q, R, S, and T peaks are visible. The P peak is more pronounced and the U peak is only visible in the ECG recorded using a graphene electrode, suggesting that the ultimate contact between graphene and skin is desirable for reading small signals.

In a second example, to measure an EMG 360 of a subject periodically squeezing a handgrip, the graphene electrode can be adhered to the forearm 220C of a subject 200 and electrical leads 310A,E are connected between the two outermost contacts 230A,E of the graphene electrode and an AVATAR™ recorder acting as the EPS test equipment 330. The EMG 360 measured using a graphene electrode and a commercially available gel electrode show comparable results.

In a third example, to measure an EEG 370 of a subject periodically opening and closing their eyes, the electrode 210 can be adhered to the forehead 220A of a subject 200 and an electrical lead can be connected to a contact on the graphene electrode. In addition, a reference electrode and a ground electrode may be adhered behind the ear and on the forearm of a subject, respectively. The electrodes may then be connected to an amplifier and BRAINVISION™ recorder software acting as the EPS test equipment. The EEG 370 measured using graphene electrodes and commercially available gel electrodes show comparable results. For example, both show a signal (~10 Hz) during rest (eyes closed).

Figure 4:
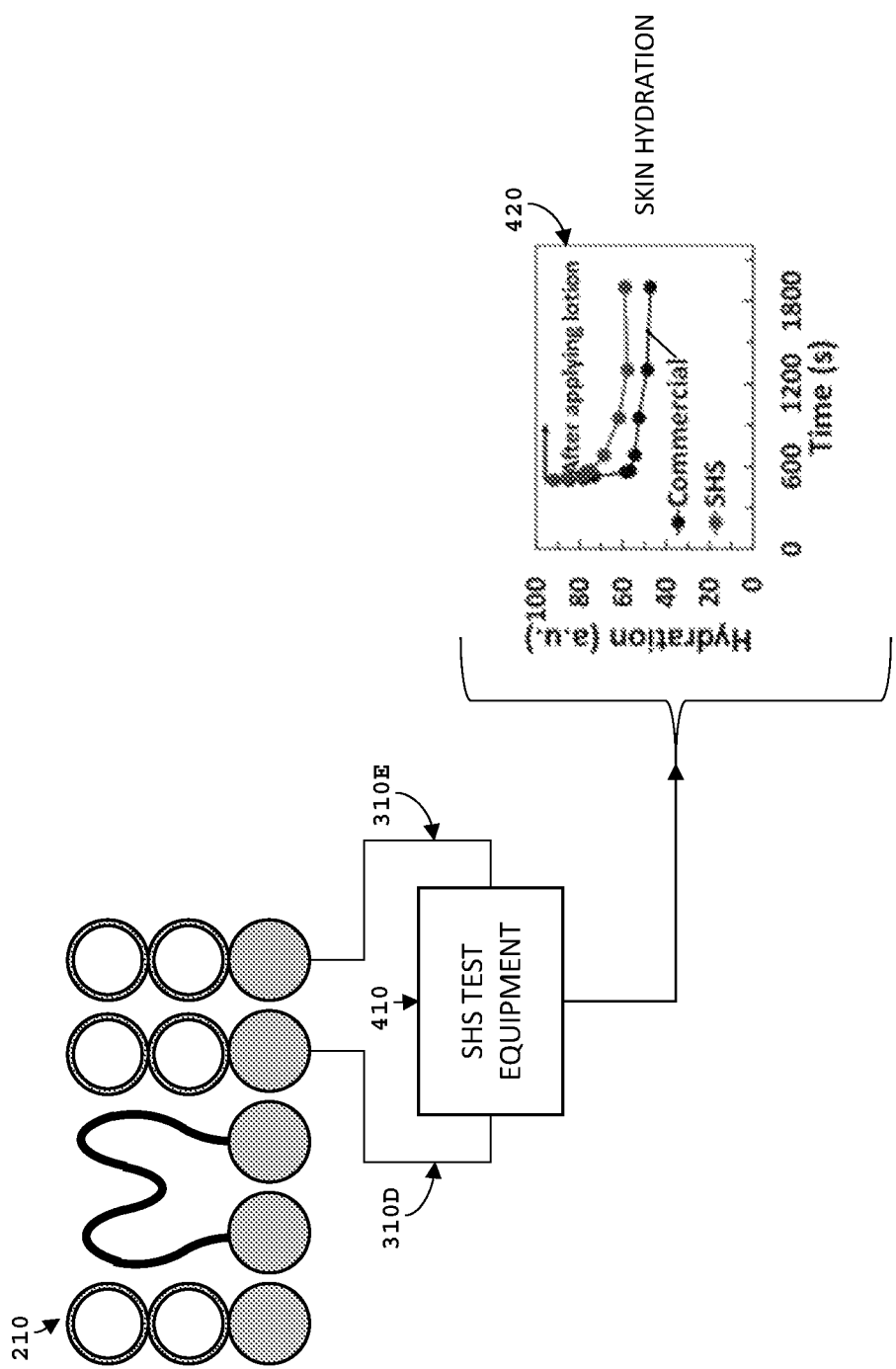
FIG. 4 graphically illustrates a graphene epidermal sensor system for measuring skin hydration according to an implementation of the present disclosure.

FIG. 4 graphically illustrates a GESS measuring skin hydration according to an implementation of the present disclosure. To measure the change in skin hydration after a subject applies skin lotion, the electrode 210 can be adhered to the forearm 220C of a subject 200 and electrical leads 310D,E can be connected between two contacts 230D,E of the graphene electrode and a LCR Meter acting as the SHS test equipment 410. A comparison of skin hydration 420 measured using a graphene electrode and a commercially available corneometer show comparable results.

Figure 5:
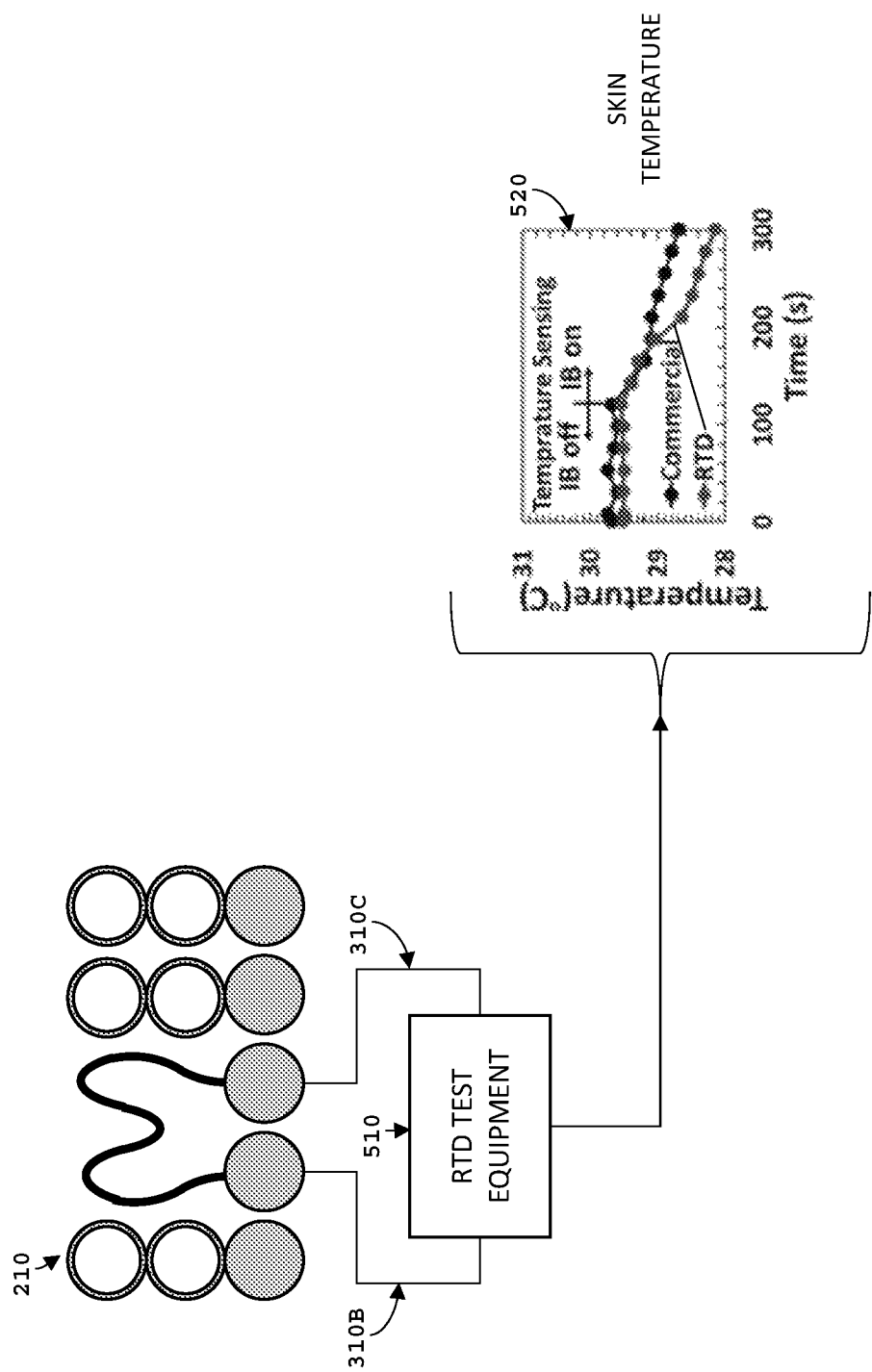
FIG. 5 graphically illustrates a graphene epidermal system for measuring skin temperature according to an implementation of the present disclosure.

FIG. 5 graphically illustrates a GESS measuring skin temperature according to an implementation of the present invention. To measure the change in skin temperature before and after the placement of an ice bag (IB) onto the skin, the electrode 210 can be adhered to the forearm 220C of a subject 200 and electrical leads 310B,C can be connected to a digital multimeter acting as the RTD test equipment 510. The digital multimeter measures the resistance of the serpentine trace connecting the pad portions of two contacts 230B,C acting as the RTD. A comparison of skin temperature 520 measured using a graphene electrode and a commercially available thermocouple show comparable results.

An additional advantage of the graphene epidermal electrode is that it can be configured in a variety of ways to allow for simultaneous measurements. For example, one or more of the above measurements may be made simultaneously. In addition, because the graphene epidermal electrode is transparent, optical tests of the electrode region are possible.

In the specification and/or figures, typical embodiments of the invention have been disclosed. The present invention is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

The invention claimed is:

1. A non-adhesive graphene epidermal sensor system (GESS), the GESS comprising:
    an epidermal electrode, the epidermal electrode comprising:
        a flexible polymer substrate coated on a first side with a monolayer of graphene that is cut into a graphene electrode pattern, wherein the graphene electrode pattern is configured to adhere to an epidermis of a test subject by a van der Waals force and be in contact with the epidermis;
        a sheet of transfer paper that is bonded to a second side of the flexible polymer substrate using a water soluble glue so that when the monolayer of graphene is placed against the epidermis of the test subject and the sheet of transfer paper is moistened, the second side of the flexible polymer substrate is released from the sheet of transfer paper and the flexible polymer substrate coated with the monolayer of graphene is adhered to the epidermis; and
        electrical leads connected to the graphene electrode pattern that transmit/receive electrical signals to/from the test subject; and
    test equipment that senses a biological parameter or measures a biological signal corresponding to the test subject, wherein the test equipment is configured to connect to the epidermal electrode using the electrical leads.

2. The GESS according to claim 1, wherein the graphene electrode pattern comprises a plurality of contacts that are spatially separated.

3. The GESS according to claim 1, wherein the graphene electrode pattern forms a skin hydration sensor (SHS).

4. The GESS according to claim 1, wherein the graphene electrode pattern forms an electrophysiological sensor (EPS).

5. The GESS according to claim 1, wherein the graphene electrode pattern remains adhered to the epidermis for a period of days and wherein the test equipment is attached to and disconnected from the epidermal electrode multiple times during the period of days.

6. A method for using a non-adhesive graphene epidermal sensor system (GESS), the method comprising:
    adhering a graphene electrode pattern to an epidermis of a subject, wherein the graphene electrode pattern comprises a plurality of contacts comprising a flexible polymer substrate coated on a first side with a monolayer of graphene, and wherein the graphene electrode pattern is adhered to the epidermis of the subject using a sheet of transfer paper that is bonded to a second side of the flexible polymer substrate using a water soluble glue so that when the graphene electrode pattern is placed against the epidermis of the test subject and the sheet of transfer paper is moistened, the second side of the flexible polymer substrate is released from the sheet of transfer paper and the graphene electrode pattern is adhered to the epidermis by a van der Waals force and in contact with the epidermis; and,
    connecting electrical leads to two or more of the plurality of contacts;
    connecting the electrical leads to test equipment;
    transmitting/receiving electrical signals to/from the electrical leads to sense an attribute of the epidermis or an electrophysiological signal using the test equipment.

7. The method according to claim 6, wherein the attribute of the epidermis is a hydration level.

8. The method according to claim 6, wherein the attribute of the epidermis is a temperature.

9. The method according to claim 6, wherein the electrophysiological signal is an electrocardiogram (ECG).

10. The method according to claim 6, wherein the electrophysiological signal is an electroencephalogram (EEG).

11. The method according to claim 6, wherein the electrophysiological signal is an electromyogram (EMG).

12. The method according to claim 6, wherein the connecting electrical leads to two or more of the plurality of contacts comprises aligning the electrical leads with one or more alignment features, wherein the alignment features are one or more shapes, patterns, and/or openings in the graphene electrode pattern.

13. The method according to claim 6, wherein the flexible polymer substrate is polyimide (PI).

* * * * *